US010913920B1

(12) United States Patent
van Buskirk et al.

(10) Patent No.: US 10,913,920 B1
(45) Date of Patent: Feb. 9, 2021

(54) FRAGRANCE CONTAINING PASTILLES

(71) Applicant: Value Smart Products, Inc., Suwanee, GA (US)

(72) Inventors: Gregory van Buskirk, Danville, CA (US); J. Drew Harrison, Suwanee, GA (US)

(73) Assignee: Value Smart Products, Inc., Suwanee, GA (US)

( * ) Notice: Subject to any disclaimer, the term of this patent is extended or adjusted under 35 U.S.C. 154(b) by 0 days.

(21) Appl. No.: 16/411,448

(22) Filed: May 14, 2019

Related U.S. Application Data

(60) Provisional application No. 62/671,272, filed on May 14, 2018.

(51) Int. Cl.

| | |
|---|---|
| ***A61L 9/04*** | (2006.01) |
| ***A61K 8/00*** | (2006.01) |
| ***C11D 3/50*** | (2006.01) |
| ***C11D 3/37*** | (2006.01) |
| ***C11D 3/04*** | (2006.01) |
| ***C11D 3/20*** | (2006.01) |
| *C11D 3/00* | (2006.01) |

(52) U.S. Cl.
CPC .............. *C11D 3/505* (2013.01); *C11D 3/048* (2013.01); *C11D 3/2079* (2013.01); *C11D 3/3707* (2013.01); *C11D 3/0068* (2013.01)

(58) Field of Classification Search
CPC ...................................................... C11D 3/505
USPC .......................................................... 512/4, 1
See application file for complete search history.

(56) References Cited

U.S. PATENT DOCUMENTS

| | | | | |
|---|---|---|---|---|
| 4,145,184 | A * | 3/1979 | Brain | C11D 3/505 8/137 |
| 5,474,698 | A | 12/1995 | Rolando et al. | |
| 5,674,831 | A | 10/1997 | Schulz et al. | |
| 5,698,513 | A | 12/1997 | Schulz et al. | |
| 6,844,302 | B1 | 1/2005 | Boden et al. | |
| 7,867,968 | B1 | 1/2011 | Aouad | |
| 7,871,976 | B1 | 1/2011 | Aouad | |
| 8,476,219 | B2 | 7/2013 | Aouad | |
| 9,453,189 | B2 | 9/2016 | Aouad | |
| 9,708,574 | B2 | 7/2017 | Aouad | |
| 2002/0137657 | A1 | 9/2002 | Lant et al. | |
| 2003/0195134 | A1 | 10/2003 | Vandijk et al. | |
| 2003/0203829 | A1 * | 10/2003 | Shefer | C11D 1/62 510/327 |
| 2004/0116317 | A1 | 6/2004 | Burt et al. | |
| 2008/0014228 | A1 | 1/2008 | Darmuzey et al. | |
| 2008/0135062 | A1 | 6/2008 | Hibbard | |
| 2008/0293615 | A1 | 11/2008 | Kieffer et al. | |
| 2009/0105111 | A1 | 4/2009 | Stolte et al. | |
| 2011/0294715 | A1 | 12/2011 | Smets et al. | |
| 2011/0301072 | A1 | 12/2011 | Smith et al. | |
| 2012/0231992 | A1 | 9/2012 | Kieffer et al. | |
| 2015/0084224 | A1 | 3/2015 | Stolte et al. | |
| 2015/0218492 | A1 | 8/2015 | Dale et al. | |
| 2015/0376550 | A1 * | 12/2015 | Ohtani | C11D 3/505 510/296 |
| 2016/0106635 | A1 | 4/2016 | Yan et al. | |
| 2017/0152462 | A1 | 6/2017 | Baltsen et al. | |
| 2018/0044616 | A1 | 2/2018 | Piorkowski | |
| 2018/0100124 | A1 | 4/2018 | Piorkowski | |
| 2018/0105766 | A1 | 4/2018 | Caparros Casco | |

* cited by examiner

*Primary Examiner* — Jessica Whiteley
(74) *Attorney, Agent, or Firm* — Edwin A. Sisson, Attorney at Law, LLC; Jeffrey Banyas

(57) ABSTRACT

A solid laundry fragrance particle to enhance the fragrance of laundry comprised of a hydrated alkali metal or alkali earth metal salt, a thickener, and a fragrance.

6 Claims, No Drawings

FRAGRANCE CONTAINING PASTILLES

This application claims priority from U.S. Provisional Patent Application No. 62/671,272 filed on 14 May 2018 the teachings of which are incorporated in their entirety.

BACKGROUND

Laundry scent boosters have become an increasingly important category within the laundry care category. In essence, these products provide additional fragrance, preferably including fragrance that released after extended periods, in addition to that provided by classic laundry products such as detergents, stain removers, and fabric softeners. It is especially preferred that these products are delivered into the washing cycle, and that they provide significant fragrance impact post-washing, while being stored before wearing, and during subsequent wear.

Numerous patents, applications, and commercial developments have provided such functionality through various vehicles. In the United States, Henkel Corporation introduced Purex Crystals in 2011, and were positioned as a fabric softener based on their development in Europe. The formulation of this product was based on sodium chloride, PEG distearate, bentonite, sodium silicate, fragrance, silica, and colorant. The production of such a formula is essentially non-molten, possibly except for application of fragrance in a PEG stearate base to otherwise solid components.

Procter and Gamble has been granted several patents describing laundry pastilles comprising polyethylene glycol, fragrance, and fragrance encapsulates (see U.S. Pat. Nos. 9,708,574 B2, 9,453,189 B2, 8,476,219 B2, 8,476,219 B2, 7,871,976 B1, and 7,867,968 B1, all to Aouad. All of these patents describe preparation of a polyethylene glycol melt, free perfume oil, and friable perfume microencapsulates. Other so-called laundry actives can be incorporated, such as detergent surfactants, detergent builders, bleaching agents, and enzymes. There is no mention of significant amounts of water, other than minor amounts that may be introduced from fragrance microcapsules, nor of functionally inert materials.

US 2018/0100124 A1 to Piorkowski (Henkel) describes solid compositions for fabric treatment (SCFT), comprising from about 50% by weight to about 99% by weight of a polyethylene glycol, a fragrance; and up to about 50% by weight of a block copolymer. Additional additives mentioned may include alkali metal salts such as sodium chloride, sodium acetate, sodium carbonate, sodium hydrogen carbonate (bicarbonate), etc., as well as alkaline earth metal salts, such as magnesium chloride and magnesium sulfate. Again, there is no mention of significant amounts of water, other than minor amounts that may be introduced from fragrance microcapsules.

Method Products has commercialized so-called fragrance boosters, comprising sodium acetate, sodium bicarbonate, fragrance, silica, polyethylene glycol, polyacrylate, tocopherol acetate (vitamin E), and colorant. There is no water that is disclosed in the composition.

It is noteworthy that none of these prior art mentions incorporation of significant levels of water, either freely or as the hydrate of a salt. Incorporation of water into such compositions during a melt stage would ordinarily compromise the integrity of such laundry scent boosters, including those derived from polymers such as polyethylene glycol and block copolymers (such as poloxamers), and especially those comprising water-soluble additives such as alkali metal and alkaline earth metal salts. We have found that by advantageous choice of ingredients, significant levels of water can be used in scent booster formulations.

SUMMARY

This specification discloses a laundry fragrancing composition comprising a first hydrated alkali metal or earth metal salt, a fragrance oil, and a microencapsulated perfume in solid form.

The specification further discloses that the composition further comprises a second alkali metal or earth metal salt which is different from the first hydrated alkali metal or earth metal salt.

It is further disclosed that the composition further comprises a polyalkylene oxide and that in some embodiments the polyalkylene oxide is a copolymer of polypropylene oxide and polyethylene oxide. In other embodiments the polyalkylene oxide can be a homopolymer of polyethylene oxide.

It is also disclosed that the total amount of water in the composition be less than or equal to the stoichiometric amount required to hydrate the alkali metal or alkaline earth metal salt in the composition.

This specification further discloses that the first hydrated alkali metal or earth metal salt can be selected from the group consisting of sodium acetate trihydrate, magnesium chloride hexahydrate, magnesium nitrate hexahydrate and magnesium sulfate heptahydrate.

The specification additionally discloses a composition for the delivery of fragrance to a washload. The composition comprising a first hydrated alkali metal or earth metal salt selected from the group consisting of sodium acetate trihydrate, magnesium chloride hexahydrate, magnesium nitrate hexahydrate and magnesium sulfate heptahydrate, wherein the first hydrated alkali metal or earth metal salt is in the range of 10 to 97 weight percent of the composition. The composition also contains a thickening agent, wherein the thickening agent is in the range of 0.1 to 10 weight percent of the composition and a fragrance, wherein the fragrance is in the range of 2 to 10 weight percent of the composition.

Optional disclosed ingredients are a co-polymer of polypropylene oxide and polyethylene oxide, wherein the co-polymer of polypropylene oxide and polyethylene oxide is in the range of 0 to 60 weight percent of the composition, polyethylene glycol, wherein the polyethylene glycol is in the range of 0 to 60 weight percent of the composition, sodium bicarbonate, wherein the sodium bicarbonate is in the range of 0 to 40 weight percent of the composition, sodium chloride, wherein the sodium chloride is in the range of 0 to 40 weight percent of the composition, wherein the weight percent of all the components total 100 weight percent; and the composition is a solid.

It is further disclosed that the total water content of the composition for the delivery of fragrance to a washload be less than or equal to the stocihiometric amount required to hydrate the alkali metal or alkali metal earth salts in the composition.

This specification further discloses a method of imparting a fragrance to laundry comprising the step of adding an amount of a composition comprised of a first hydrated alkali metal or earth metal salt selected from the group consisting of sodium acetate trihydrate, magnesium chloride hexahydrate, magnesium nitrate hexahydrate and magnesium sulfate heptahydrate, wherein the first hydrated alkali metal or earth metal salt is in the range of 10 to 97 weight percent of the composition; a thickening agent, wherein the thickening agent is in the range of 0.1 to 10 weight percent of the composition, a fragrance, wherein the fragrance is in the range of 2 to 10 weight percent of the composition.

The composition used in the method could optionally contain a co-polymer of polypropylene oxide and polyethylene oxide, wherein the co-polymer of polypropylene oxide and polyethylene oxide is in the range of 0 to 60 weight percent of the composition, polyethylene glycol, wherein the polyethylene glycol is in the range of 0 to 60 weight percent of the composition, sodium bicarbonate, wherein the sodium bicarbonate is in the range of 0 to 40 weight percent of the composition, sodium chloride, wherein the sodium chloride is in the range of 0 to 40 weight percent of the composition, wherein the weight percent of all the components total 100 weight percent and the composition is a solid and that composition is added to an aqueous mixture comprising fabrics.

DETAILED DESCRIPTION

The presently disclosed embodiments, as well as features and aspects thereof, are directed towards a composition comprising, or consisting essentially of, or consisting of a plurality of hydrates of alkali metal or alkaline earth metal salts. The melting point of such hydrated salts should be less than 150° C., preferably less than 125° C., most preferably less than 100° C. Especially preferred are hydrated salts with melting points below 60° C.

It has been surprisingly discovered that the use of hydrates in the molten mixture before adding the fragrance allows the mixture to be kept at a much lower temperature that using the anhydrous version of the salt.

Examples of such hydrated salts include but are not limited to sodium acetate trihydrate (melting point 58° C.), magnesium nitrate hexahydrate (melting point 89° C.), magnesium chloride hexahydrate (melting point 117° C.), and magnesium sulfate heptahydrate (also known as Epsom salt, melting point 150° C.). In the final composition, it is foreseen that water would comprise at least 5% of the final product, preferably at least 10%, and most preferably at least 20% of the composition.

Also envisioned are of additives that include an additional salts, such as alkali metal or alkaline earth metal salts of acetate, bicarbonate, carbonate, chloride, nitrate, or sulfate, polymers such as polyethylene glycol, copolymers of polyethylene oxide and polypropylene oxide (i.e., poloxamers), PET-100 Stearate or Steareth-100, as well as urea, and a laundry fragrance. The composition may be in shaped form, e.g., a pastille, a granulate, an agglomerate, or a spheroid formed from of concentric laying of ingredients.

In all the embodiments, all the weight percent of all components of the embodiment total 100 wt % of the composition.

Acetate salts may be a Group I acetate salt, e.g., a lithium, a sodium, and/or a potassium acetate. The acetate salt is typically used in solid form, e.g., anhydrous or in hydrated form, or hydrated polymorphs. For example, sodium acetate monohydrate, dihydrate, and/or trihydrate may be used. The acetate salt may be anhydrous and added to an aqueous composition having less than stoichiometric amount of water required to hydrate the salt. Alternatively, the acetate salt may hydrated when added to the composition. The amount of acetate salt by weight of the composition may be from about 10% to about 97%, or from about 10% to about 95%, or from about 15% to about 90%, or from about 20% to about 85%, or from about 30% to about 80%, or from about 40% to about 70% or from about 45% to about 60%. Sodium acetate is available from multiple vendors, including Brenntag North America, Inc., Reading, Pa.; Jarchem Industries, Inc., Newark, N.J.; and Pacific Coast Chemicals Company, Vernon, Calif.

Sodium bicarbonate is typically used in solid form, e.g., anhydrous or in hydrated form, or hydrated polymorphs. Sodium bicarbonate may be part of an aqueous composition. If included, the amount of sodium bicarbonate by weight of the composition may be from about 5% to about 55%, or from about 5% to about 40%, or from about 10% to about 30%, or from about 15% to about 25%. Sodium bicarbonate is available from multiple vendors, including Brenntag North America, Inc., Reading, Pa.; Solvay USA, Inc., Princeton, N.J.; and Univar, Downer Grove, Ill.

Sodium chloride is typically used in solid form, e.g., anhydrous or in hydrated form, or hydrated polymorphs. Sodium chloride may be part of an aqueous composition (e.g., a brine). If included, the amount of sodium chloride by weight of the composition may be from about 10% to about 55%, or from about 10% to about 40%, or from about 10% to about 30%, or from about 15% to about 25%. Sodium chloride is available from multiple vendors, including Brenntag North America, Inc., Reading, Pa.; Cargill, Inc., Wayzota, Minn.; and Morton Salt, Inc., Chicago, Ill.

A copolymer of propylene oxide (PO) and ethylene oxide (EO) is typically used in solid form. They may be randomly assembled units of polyethylene oxide and polypropylene oxide, or so-called block copolymers wherein units of two or more polypropylene oxide subunits are linked by covalent bonds to one or more polyethylene oxide subunits.

Particularly useful are PEO-PPO-PEO block copolymers, wherein one or more subunits of polypropylene oxide (PPO) are surrounded by one or more subunits of polyethylene oxide (PEO). Such copolymers are particularly useful not only for their ability to help pastille formation, but to impart a defoamer to the laundry wash liquor. This is particularly useful in so-called high-efficiency washers, where foaming can be deleterious to the functioning of the washing machine. The PPO/PEO copolymer may be of a non-random configuration and number-averaged molecular weight that results in it being solid at room temperature, and more preferably remains solid in conditions that are experienced throughout the process of being distributed to the consumer. The PPO/PEO copolymer may be of a number-averaged molecular weight above 4000, or above 10000, or above 15000, or from about 4000 to about 15000 or from about 6000 to about 15000 or from about 8000 to about 15000, or from about 10000 to about 15000. If included, the amount of copolymer of propylene oxide and ethylene oxide by weight of the total composition may be from about 5% to about 90%, or from about 10% to about 50%, or from about 15% to about 25%. PPO/PEO copolymer is available from multiple vendors, including BASF, Ludwigshafen, Germany under the tradename Pluronic™.

Polyethylene oxide, also known as polyethylene glycol ("PEG"), may be safe for human consumption, e.g., substantially non-toxic, e.g., a medically acceptable PEG identified as CAS Reg. No. 25322-68-3. The PEG may be of a number-averaged molecular weight that results in it being solid at room temperature, and more preferably remains solid in conditions that are experienced throughout the process of being distributed to the consumer. The PEG may be of number-averaged molecular weight above 2000, or above 3350, or above 4000, or from about 2000 to about 4000 or from about 3000 to about 4000 or from about 3000 to about 5000, or from about 4000 to about 5000. If included, the amount of copolymer of propylene oxide and ethylene oxide by weight of the composition may be from about 5% to about 40%, or from about 10% to about 30%, or from about 15% to about 25%. Polyethylene glycol is available from multiple vendors, including Brenntag North America, Inc., Reading, Pa. Clariant Industrial & Home Care, Muttenz, Switzerland under the tradename Polyglykol™, and Dow Chemical Company, Midlands, Mich. under the tradename Carbowax™.

The fragrance may be a fragrance oil. Fragrance oils are available from multiple vendors, such as Berjé, Cateret, N.J.; Firmenich, Geneva, Switzerland; Givaudan, Vernier, Switzerland; International Flavors & Fragrances, New York, N.Y.; and Symrise, Holzminden, Germany.

The fragrance may also comprise a perfume microencapsulate or microcapsule. By the term perfume microencapsulate or microcapsule is meant those microcapsules described in US Patent Publication 2013/0267454 A1, incorporated herein in its entirety.

In an embodiment, the composition may comprise from about 2% to about 12% by weight of the fragrance; and/or from about 2% to about 12% by weight of the perfume microcapsule. In another embodiment, the fragrance may be about 2, 3, 4, 5, 6, 7, 8, 9, 10, 11 or 12 percent by weight of the product, or may be in a range from about one integer to about another integer in the forgoing integer listing, e.g., from about 2 to about 9 percent by weight of the total composition. In another embodiment, the perfume microcapsule may be about 2, 3, 4, 5, 6, 7, 8, 9, 10, 11 or 12 percent by weight of the composition, or may be in a range from about one integer to about another integer in the forgoing integer listing, e.g., from about 2 to about 9 percent by weight of the total composition.

In an embodiment, the composition may comprise a compound that imparts thickening to the molten composition. Preferred thickening compounds include a carbohydrate, or a complex carbohydrate that is different than the PEO/PPO copolymer or PEG polymer described above. Examples include gums, starches, or other natural or synthetic polymers, e.g., carrageenan, Xanthan gum, alginates, and vegetable-based starches, e.g. cornstarch.

The composition is suitable to impart a fragrance to laundry (or act as a "scent booster") that is processed by hand, by machine, or by association. For example, about 5 grams (g) to about 100 g, or about 5 g to about 50 g, or about 5 g to about 25 g of composition may be used in a domestic, non-commercial washing machine load per 10-20 pounds of laundry. The composition may be used in front-loading, e.g., high efficiency washers (about 10-25 gallons water per load) or in top-loading washers (about 40-50 gallons water per load). The method of imparting the fragrance is effected by adding the composition to the washing machine load at a point in the machine cycle when water is present, e.g., during cleaning and/or rinsing phases.

The composition is preferably delivered to the laundry in solid form, more preferably as discrete particles, most preferably as uniform, similarly sized and shapped particles. Such particles can be produced via spray drying, tableting, or most preferably through pastillation. During processing, the composition may be uniformly molten, or handled as a dispersed slurry wherein the solid components are small enough to be capable of passing through the process without clogging small holes (as may be encountered in a pastillator).

Water may be present in the solid composition, either as part of a hydrate of an inorganic salt described above, or bound as part of an organic thickening system described above.

It has also been discovered that the composition can be made by adding the anyhydrous salt(s) and water to the composition before the adding the fragrance. The water will hydrate the salt(s), provided that the amount of water added is less than the stoichiometric amount of water required to hydrate the salt(s).

EXAMPLES

EXAMPLE 1: In one embodiment, about 53 g sodium acetate trihydrate, about 35 g water, about 2 g thickener, and about 2 g calcium chloride are admixed and heated to about 160° F. (about 71° C.) while agitating the mixture in a vessel until the ingredients appear visually well-dispersed, e.g., in a viscous, semi-translucent liquid. The mixture temperature is allowed to drop to about 150° F. (about 66° C.) during agitation, followed by adding 3 g fragrance oil, and 5 g microencapsulated perfume.

The molten admixture is then pastillated to deposit tear-drop-shaped liquid aliquots on a moving cooled belt. When dropped on the belt, the aliquot will become circular with concave top and flat at the belt side. The belt is maintained at about 60° F. (about 15° C.) to allow the aliquots to harden to waxy pastilles. The pastilles are then removed from the belt and are ready for use. The product is soluble within the time of the wash and/or rinse cycle of a laundering process, and has a final melting point of about 58° C. The final amount of water in the solid composition is 35%.

EXAMPLE 2: In an embodiment, about 48 g sodium acetate trihydrate, about 24 g sodium bicarbonate, about 17 g of a co-polymer of propylene oxide and ethylene oxide, and about 2 g corn starch are admixed and heated to about 160° F. (about 71° C.) while agitating the mixture in a vessel until the ingredients appear visually well-dispersed, e.g., in a viscous, semi-translucent liquid. The mixture temperature is allowed to drop to about 150° F. (about 66° C.) during agitation, followed by adding 3 g fragrance oil, and 5 g microencapsulated perfume.

The molten admixture is then pastillated to deposit tear-drop-shaped liquid aliquots on a moving cooled belt. The belt is maintained at about 60° F. (about 15° C.) to allow the aliquots to harden to waxy pastilles. The pastilles are then removed from the belt and are ready for use. The product is soluble within the time of the wash and/or rinse cycle of a laundering process, and has a final melting point above 50° C., and or above 55° C. The final amount of water in the solid composition, whether hydrated or free, is 19%.

EXAMPLE 3: In an embodiment, about 48 g sodium acetate trihydrate, about 24 g sodium bicarbonate, about 17 g polyethylene glycol 3350, and about 2 g corn starch are admixed and heated to about 160° F. (about 71° C.) while agitating the mixture in a vessel until the ingredients appear visually well-dispersed, e.g., in a viscous, semi-translucent liquid. The mixture temperature is allowed to drop to about 150° F. (about 66° C.) during agitation, followed by adding 3 g fragrance oil, and 5 g microencapsulated perfume. The final amount of water in the solid composition is 19%.

The molten admixture is then pastillated to deposit tear-drop-shaped liquid aliquots on a moving cooled belt. The belt is maintained at about 60° F. (about 15° C.) to allow the aliquots to harden to waxy pastilles. The pastilles are then removed from the belt and are ready for use. The product solubilizes within the time of the wash and/or rinse cycle of a laundering process, and has a final melting point of about 58° C.

EXAMPLE 4: In an embodiment, about 54 grams of anhydrous sodium acetate, 35.4 grams of water, 2.5 grams of propylene glycol, 0.25% of Xanthan gum are heated to about 160° F. until uniformly mixed, after which 5.0 grams of encapsulate fragrance and 3 grams of fragrance oil are added. The molten admixture is then pastillated to deposit teardrop-shaped liquid aliquots on a moving cooled belt. The belt is maintained at about 60° F. (about 15° C.) to allow the aliquots to harden to solid pastilles. The pastilles are then removed from the belt and are ready for use. The product is soluble within the time of the wash and/or rinse cycle of a laundering process, and has a final melting point of about 58° C. The final amount of water in the solid composition, whether free or as a hydrate, is 35%. This example demonstrates the ability to hydrate the alkali metal salt in situ during the preparation of the composition.

EXAMPLE 5: In an embodiment, about 55.5 grams of PEG-100 stearate and 37 grams of magnesium nitrate hexahydrate are heated to about 190° F. until uniformly mixed, after which 5.0 grams of encapsulate fragrance and 2.5 grams of fragrance oil are added. The molten admixture is then pastillated to deposit teardrop-shaped liquid aliquots on a moving cooled belt. The belt is maintained at about 60° F. (about 15° C.) to allow the aliquots to harden to solid pastilles. The pastilles are then removed from the belt and are ready for use. The product is soluble within the time of the wash and/or rinse cycle of a laundering process, and has a final melting point above above 50° C., and or above 55° C. The final amount of water in the solid composition is 15.5%.

Therefore, although selected aspects have been illustrated and described in detail, it will be understood that various substitutions and alterations may be made therein without departing from the spirit and scope of the present invention, as defined by the following claims.

We claim:

1. A laundry fragrancing composition comprising a first hydrated alkali metal or alkaline earth metal salt, a fragrance oil which is not microencapsulated, and a microencapsulated perfume, wherein the composition is in solid form at 15° C. and the first hydrated alkali metal or alkaline earth metal salt is selected from the group consisting of sodium acetate trihydrate, magnesium chloride hexahydrate, magnesium nitrate hexahydrate and magnesium sulfate heptahydrate.

2. The composition of claim 1 wherein the composition further comprises a second alkali metal or alkaline earth metal salt which is different from the first hydrated alkali metal or alkaline earth metal salt.

3. The composition of claim 1 wherein the composition further comprises a polyalkylene oxide.

4. The composition of claim 3 wherein the polyalkylene oxide is a copolymer of polypropylene oxide and polyethylene oxide.

5. The composition of claim 3 wherein the polyalkylene oxide is a homopolymer of polyethylene oxide.

6. The composition of claim 1 wherein the amount of water in the composition is less than or equal to the stoichiometric amount required to hydrate the alkali metal or alkaline earth metal salt in the composition.

* * * * *